(12) United States Patent
Schleicher et al.

(10) Patent No.: US 8,357,145 B2
(45) Date of Patent: Jan. 22, 2013

(54) IMPLANTING MEDICAL DEVICES

(75) Inventors: Brett Schleicher, Valencia, CA (US); Rafael Carbunaru, Studio City, CA (US); Kristen N. Jaax, Santa Clarita, CA (US); Todd K. Whitehurst, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1336 days.

(21) Appl. No.: 11/938,740

(22) Filed: Nov. 12, 2007

(65) Prior Publication Data
US 2009/0125088 A1 May 14, 2009

(51) Int. Cl.
*B43L 13/20* (2006.01)
(52) U.S. Cl. ............ 606/1; 378/162; 378/163; 378/164; 378/165; 378/204; 378/205; 378/207; 600/414; 600/426; 33/511; 33/512; 33/566
(58) Field of Classification Search .................. 606/1
See application file for complete search history.

(56) References Cited

U.S. PATENT DOCUMENTS

| | | | |
|---|---|---|---|
| 5,193,539 A | 3/1993 | Schulman et al. | |
| 5,193,540 A | 3/1993 | Schulman et al. | |
| 5,312,439 A | 5/1994 | Loeb | |
| 5,324,316 A | 6/1994 | Schulman et al. | |
| 5,405,367 A | 4/1995 | Schulman et al. | |
| 6,051,017 A | 4/2000 | Loeb et al. | |
| 6,356,621 B1 * | 3/2002 | Furumori et al. | 378/162 |
| 6,520,916 B1 | 2/2003 | Brennen | |
| 6,678,546 B2 | 1/2004 | Toker et al. | |
| 6,818,291 B2 | 11/2004 | Funkenbusch et al. | |
| 7,127,826 B2 * | 10/2006 | Russell | 33/758 |
| 7,261,950 B2 | 8/2007 | Fleming et al. | |
| 7,351,479 B2 | 4/2008 | Funkenbusch et al. | |
| 7,602,883 B2 * | 10/2009 | Joseph et al. | 378/162 |
| 2002/0103431 A1 | 8/2002 | Toker et al. | |
| 2003/0092995 A1 | 5/2003 | Thompson | |
| 2004/0033384 A1 | 2/2004 | Funkenbusch et al. | |
| 2005/0245806 A1 | 11/2005 | Singhal et al. | |
| 2005/0247470 A1 | 11/2005 | Fleming et al. | |
| 2006/0035073 A1 | 2/2006 | Funkenbusch et al. | |

(Continued)

FOREIGN PATENT DOCUMENTS

| | | |
|---|---|---|
| WO | WO 98/37926 | 9/1998 |
| WO | WO 98/43700 | 10/1998 |

(Continued)

OTHER PUBLICATIONS

Tracy Cameron et al., "Micromodular Implants to Provide Electrical Stimulation of Paralyzed Muscles and Limbs,"in IEEE Transactions on Biomedical Engineering, vol. 44, No. 9, Sep. 1997, pp. 781-790.

*Primary Examiner* — Aaron Roane
(74) *Attorney, Agent, or Firm* — Frommer Lawrence & Haug; Bruce E. Black (57) ABSTRACT

Systems and techniques for implanting medical devices. In one aspect, an apparatus includes a flexible base member that can be flexed manually to conform to a contour of an anatomy, the base member including a radioscopic indicium that has a characteristic such that, under radioscopic imaging, passage of a skin-penetrating electromagnetic radiation is hindered to an extent that is distinguishable from a hindrance of the electromagnetic radiation by another portion of the base member.

21 Claims, 9 Drawing Sheets

U.S. PATENT DOCUMENTS

| | | |
|---|---|---|
| 2006/0142801 A1* | 6/2006 | Demarais et al. ............... 607/2 |
| 2007/0265499 A1 | 11/2007 | Wood et al. |
| 2008/0147059 A1 | 6/2008 | Bee et al. |

FOREIGN PATENT DOCUMENTS

| | | |
|---|---|---|
| WO | WO 98/43701 | 10/1998 |
| WO | WO 02/09587 A2 | 2/2002 |
| WO | WO 02/060316 A2 | 8/2002 |
| WO | WO 03/073942 A2 | 9/2003 |
| WO | WO 2004/017699 A1 | 2/2004 |
| WO | WO 2004/017700 A1 | 2/2004 |
| WO | WO 2004/017701 A2 | 2/2004 |
| WO | WO 2007/130720 A1 | 11/2007 |
| WO | WO 2008/064111 A2 | 5/2008 |

* cited by examiner

IMPLANTING MEDICAL DEVICES

BACKGROUND

This disclosure relates to implanting medical devices.

SUMMARY

Systems and techniques for implanting medical devices are described. In one aspect, an apparatus for implanting a medical device includes a flexible base member that can be flexed manually to conform to a contour of an anatomy, the base member including a radioscopic indicium that has a characteristic such that, under radioscopic imaging, passage of a skin-penetrating electromagnetic radiation is hindered to an extent that is distinguishable from a hindrance of the electromagnetic radiation by another portion of the base member.

This and other aspects can include one or more of the following features. The base member can include an illustration of the medical device. The illustrated medical device can include a charging element for accumulating potential energy at the medical device. The medical device illustration can include a marking selected to correspond to feature found on the medical device. The base member can include a sheet-like polymeric material. The apparatus can include an adhesive to removably adhere the base member to the contour of the anatomy.

The base member can also include a visual indicium that is visible to a naked eye and is positioned on the base so that when the visual indicium is properly arranged relative to an anatomical feature of a patient, the base can guide the implantation of the medical device. The apparatus can also include a surgical cutout that spans the base member and is positioned on the base member to identify an anatomical location that is relevant to an implantation when the base member is properly arranged. The radioscopic indicium can demarcate the position of the surgical cutout under radioscopic imaging.

The apparatus can also include an alignment tab that extends outward from the base member and that is dimensioned so that when the alignment tab is properly arranged relative to an anatomical feature of a patient. The base can guide the implantation of the medical device. The radioscopic indicium can be positioned on the base so that when the radioscopic indicium is properly arranged relative to an anatomical feature of a patient, the base can guide the implantation of the medical device. The radioscopic indicium can be positioned on the base to guide the implantation of the medical device.

In another aspect, a system includes a medical device that includes a charging element for accumulating potential energy at a medical device and a base member that can be flexed manually to conform to a contour of an anatomy, the base member including a radioscopic indicium that, under radioscopic imaging, hinders passage of a skin-penetrating electromagnetic radiation to an extent that is distinguishable from a hindrance of the electromagnetic radiation by another portion of the base member.

This and other aspects can include one or more of the following features. The charging element can include a charging coil.

In another aspect, a method includes arranging an apparatus for implanting a medical device relative to an anatomical feature and implanting, under guidance of the apparatus, the medical device. The apparatus for implanting the medical device includes one or more of a visual indicium that is visible to a naked eye and a radioscopic indicium that, under radioscopic imaging, hinders passage of a skin-penetrating electromagnetic radiation to an extent that is distinguishable from a hindrance of the electromagnetic radiation by another portion of the apparatus. The one or more indicia are positioned on the apparatus to guide implantation of the medical device. The medical device includes a charging element for accumulating potential energy at the medical device and the guidance of the apparatus arranges the charging element for the effective accumulation of the potential energy.

This and other aspects can include one or more of the following features. The apparatus can be flexed manually to conform to a contour of an anatomy. Implanting the medical device under the guidance of the apparatus can include radioscopically imaging the medical device and the radioscopic indicium of the apparatus. For example, the medical device can be radioscopically imaged to confirm that the charging element is arranged properly.

The apparatus can be arranged to align the visual indicium with the anatomical feature and/or to align a mechanical element with the anatomical feature. For example, an outwardly-extending arm can be contacted to the anatomical feature. Arranging the apparatus can also include aligning, with the anatomical feature, a preformed, solid element that retains a shape.

The details of one or more implementations are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Figure 1:
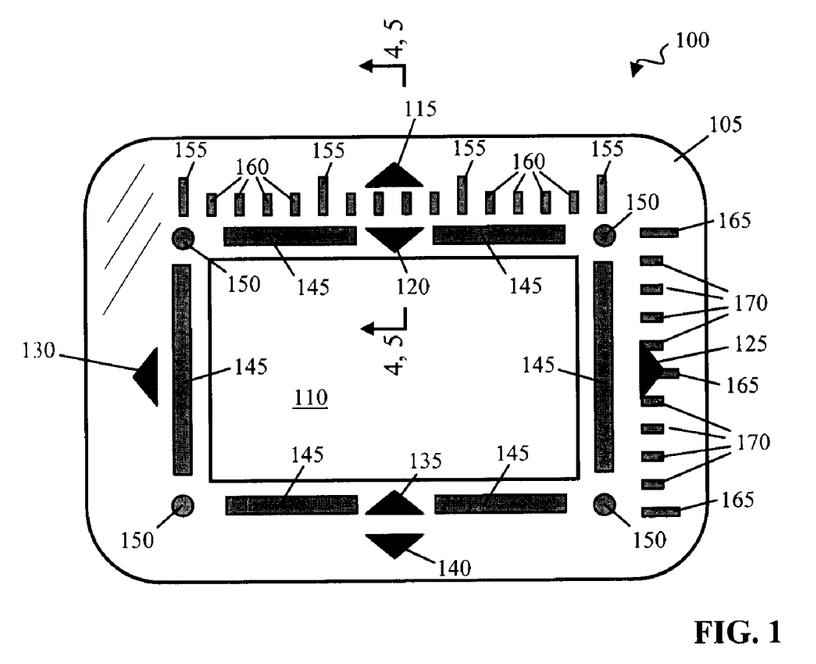
FIGS. 1, 2, 3, 6 are schematic representations of apparatus for implanting one or more medical devices.

FIG. 1 is a schematic representation of an apparatus 100 for implanting one or more medical devices. Apparatus 100 includes a sterile, sheet-like base 105 that includes markings, patterns, and other indicia to indicate the proper placement and alignment of a medical device to medical personnel. Base 105 can be positioned to align indicia thereon with anatomical features of a patient and/or a medical device during or after implantation. Medical personnel can rely upon the arrangement of base 105 to ensure that the positioning and alignment of the medical device is proper.

In the illustrated implementation, base 105 defines a surgical cutout 110 and includes both visual indicia 115, 120, 125, 130, 135, 140 and radioscopic indicia 145, 150, 155, 160, 165, 170. Surgical cutout 110 traverses base 105 and, when base 105 is properly positioned, can identify an anatomical location that is relevant to an implantation. For example, surgical cutout 110 can be dimensioned and positioned to allow medical personnel to implant a medical device therethrough, e.g., by allowing medical personnel to incise skin underlying base 105 or penetrate the skin using minimally invasive surgical devices. As another example, surgical cutout 110 can be dimensioned and positioned to allow medical personnel to mark the skin of the a patient.

Visual indicia 115, 120, 125, 130, 135, 140 are markings on base 105 that are visible to the naked eye. Some visual indicia can be arranged on base 105 so that when they are properly positioned relative to anatomical features of a patient, base 105, cutout 110, and indicia thereon guide medical personnel in the proper implantation of one or more medical devices. The indicia on base 105 that guide medical personnel in the proper implantation can be visual and/or radioscopic indicia.

In some implementations, visual indicia 115, 120, 135, 140 can be dimensioned and arranged to be positioned relative to the midline of the dorsal side of the neck of a patient before, during, or after a proper implantation. Visual indicia 125, 130 can be dimensioned and arranged to be positioned relative to the intermastoid line on the dorsal side of the neck at the base of the head of a patient before, during, or after a proper implantation. Visual indicia can be dimensioned and arranged to be positioned relative to the external occipital protuberance of the head of a patient before, during, or after a proper implantation. Such a positioning of visual indicia 115, 120, 125, 130, 135, 140 can position and align base 105 for proper implantation of one or more medical devices. In general, visual indicia 115, 120, 125, 130, 135, 140 can be transparent to x-rays or other skin-penetrating electromagnetic radiation, but this is not necessarily the case.

Radioscopic indicia 145, 150, 155, 160, 165, 170 are markings on base 105 that hinder or prevent the passage of x-rays or other skin-penetrating electromagnetic radiation. For example, radioscopic indicia 145, 150, 155, 160, 165, 170 can be radiopaque. Radioscopic indicia 145, 150, 155, 160, 165, 170 can made from materials such as lead, bismuth, barium, tungsten, platinum, tantalum, gold, their alloys, and the like. Radioscopic indicia can be dimensioned and arranged on base 105 so that when they are properly positioned relative to anatomical features of a patient, base 105, cutout 110, and indicia thereon guide medical personnel in the proper implantation of one or more medical devices. The indicia on base 105 that guide medical personnel in the proper implantation can be visual and/or radioscopic indicia.

Radioscopic indicia 145 can be a set of lines that demarcate the edges of surgical cutout 110 under radioscopic imaging. Radioscopic indicia 150 can be a set of dots that demarcate the corners of surgical cutout 110 under radioscopic imaging. Radioscopic indicia 155, 160 can be sets of ruler marks that demarcate distance along the intermastoid line on the dorsal side of the neck of a patient when visual indicia 125, 130 are properly positioned relative to the intermastoid line. Radioscopic indicia 165, 170 can be sets of ruler marks that demarcate distance along the midline of dorsal side of the neck of a patient when visual indicia 115, 120, 135, 140 are properly positioned relative to the midline. In general, radioscopic indicia 145, 150, 155, 160, 165, 170 are also visible to the naked eye, although this is not necessarily the case. For example, radioscopic indicia 145, 150, 155, 160, 165, 170 can be embedded in an opaque base 105.

Figure 2:
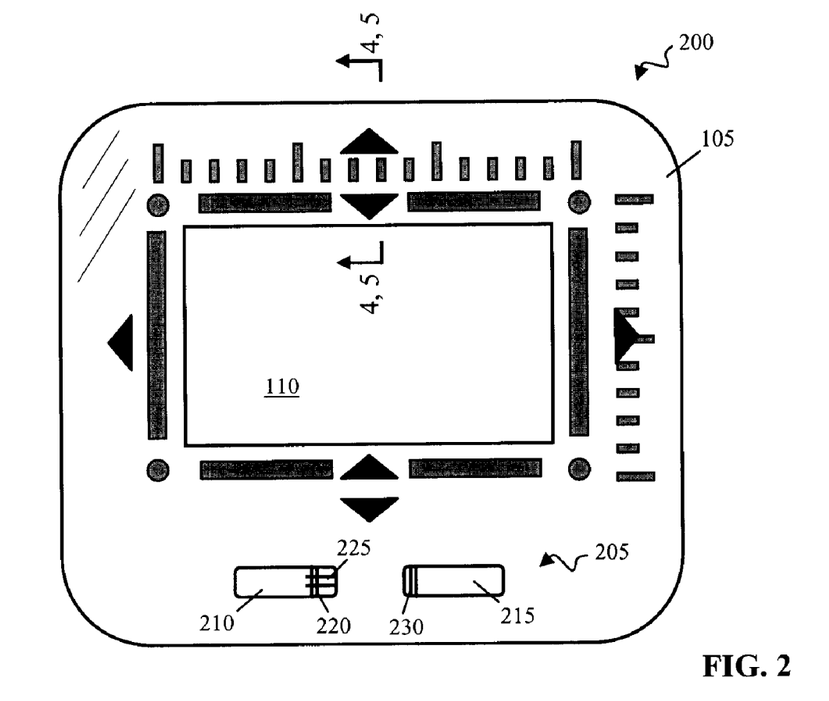

FIG. 2 is a schematic representation of an apparatus 200 for implanting one or more medical devices. In addition to base 105, cutout 110, and various visual and radioscopic indicia, apparatus 200 also includes a diagram 205 of one or more properly implanted medical devices. Diagram 205 is visible to the naked eye and can illustrate the proper arrangement of medical devices before, during, or after implantation to medical personnel.

The illustrated diagram 205 includes a representation 210 of a first medical device and a representation 215 of a second medical device. The medical devices represented by representations 210, 215 can be, e.g., microstimulators such as the BION microstimulator developed by Advanced Bionics (Sylmar, Calif.). The standard BION is a leadless microstimulator and is a cylinder that is about 3 mm in diameter and between about 2 and 3 cm in length. This form factor allows the BION to be implanted with relative ease and rapidity, e.g., via endoscopic or laparoscopic techniques. In some implementations, the BION consists of only two electrodes: a reference, or indifferent, electrode at one end and an active electrode at the other end. Various features and details associated with the manufacture, operation, and use of BION implantable microstimulators are described in U.S. Pat. No. 5,193,539, U.S. Pat. No. 5,193,540, U.S. Pat. No. 5,312,439, U.S. Pat. No. 5,324, 316, U.S. Pat. No. 5,405,367, U.S. Pat. No. 6,051,017, PCT Publication No. WO 98/37926, PCT Publication No. WO 98/43700, PCT Publication No. WO 98/43701, and the publication entitled "Micromodular Implants to Provide September Electrical Stimulation of Paralyzed Muscles and Limbs" by Cameron, et al. in IEEE Transactions on Biomedical Engineering, Vol. 44, No. 9, pages 781 790 (1997), the contents of all of which are incorporated herein by reference.

Representation 210 includes a first set of markings 220 and a second set of markings 225. Representation 215 includes a set of markings 230. Marking sets 220, 225, 230 can be selected to correspond to selected markings or other features found on the first and second medical device (not shown). Marking sets 220, 225 can be designed so that medical personnel can identify, align, and position the first medical device by mimicking the alignment and position of marking sets 220, 225 with the first medical device. Marking set 230 can be designed so that medical personnel can also align and position such a second medical device by mimicking the alignment and position of marking set 230 with the second medical device.

In some implementations, apparatus 200 can be adapted to illustrate the proper arrangement of a charging element of a medical device after implantation. A charging element is a device that participates in the accumulation of potential energy at a medical device. One example of a charging element is a conducting coil that can respond to a magnetic or electrical field generated outside a patient's body. Another example of a charging element is a photovoltaic cell that can respond to light or other electromagnetic radiation generated outside the body. Yet another example of a charging element is a mechanical element such as a piezoelectric resonator that can respond to acoustic oscillations or other mechanical disturbance generated outside the body. Proper arrangement of a charging element can help ensure that post-implantation charging of a medical device is effective.

Diagram 205 of apparatus 200 can be adapted to illustrate proper arrangement of a charging element after implantation. For example, a charging element (and/or a device that includes a charging element) can be illustrated in representations 210, 215. As another example, proper alignment of a charging element (and/or a device that includes a charging element) can be identified from marking sets 220, 225, 230.

In some implementations, apparatus 200 can be adapted to illustrate the proper arrangement of one or more electrode leads of a leaded stimulator after implantation. Electrode leads are insulated conductors that carry electrical current from a device to one or more electrode. In some implementations, electrode leads can be illustrated in representations 210, 215. As another example, proper alignment of electrode leads can be identifiable from marking sets 220, 225, 230.

In some implementations, apparatus 200 can be adapted to illustrate the location of a target for electrical stimulation. For example, the location of nerves such as the occipital nerves can be illustrated. In some implementations, apparatus 200 can also provide visual and radioscopic guides for the placement of leads, devices, needles or percutaneous electrodes, RF ablation needles, and the like relative to a target for stimulation.

Figure 3:
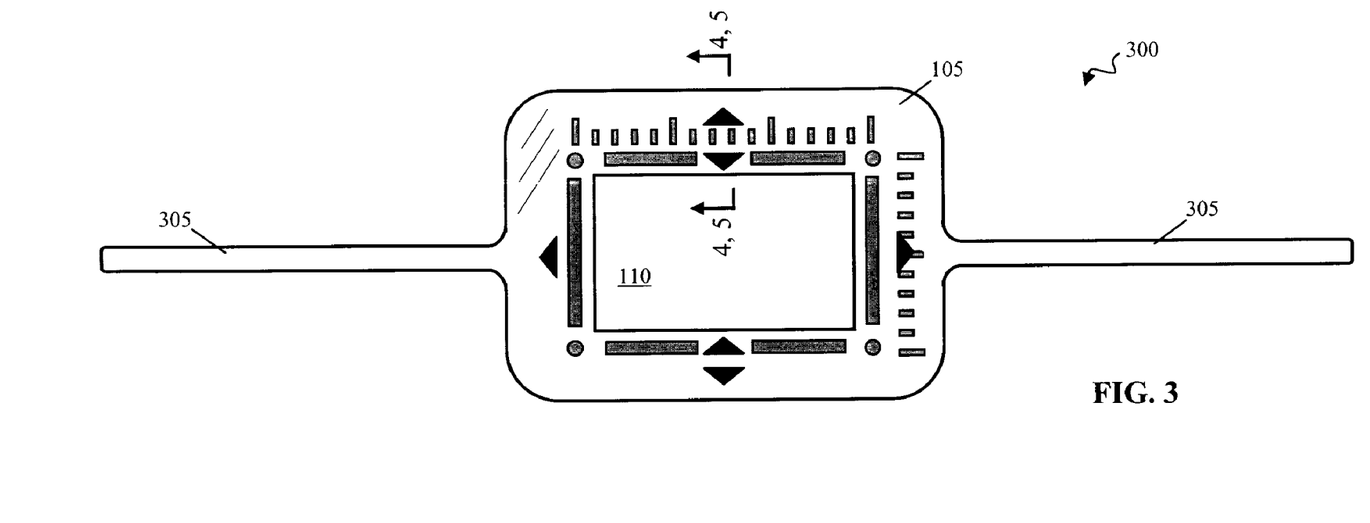

FIG. 3 is a schematic representation of an apparatus 300 for implanting one or more medical devices. In addition to base 105, cutout 110, and various visual and radioscopic indicia, apparatus 300 can also include a pair of alignment tabs 305. Alignment tabs 305 are mechanical elements that are aligned and dimensioned so that proper arrangement of tabs 305 relative to anatomical features positions base 105, cutout 110, and indicia thereon to guide medical personnel in the proper implantation of one or more medical devices. For example, alignment tabs 305 can be aligned and dimensioned to extend outwardly away from base 105 so that when alignment tabs 305 are arranged to contact the mastoid processes of a patient, base 105, cutout 110, and indicia thereon can guide medical personnel in the proper implantation of one or more medical devices in the dorsal side of the neck of a patient. As another example, alignment tabs 305 can be aligned and dimensioned to extend outwardly away from base 105 so that when alignment tabs 305 are arranged to contact the external occipital protuberance of a patient and the spinal process on the vertebrae in the neck, base 105, cutout 110, and indicia thereon can guide medical personnel in the proper implantation of one or more medical devices in the dorsal side of the neck of a patient.

In some implementations, alignment tabs 305 are formed from the same sheet-like material as base 105. For example, alignment tabs 305 and base 105 can be formed from a flexible sheet that medical personnel can manually conform to the contours of a patient's anatomy.

Figure 4:
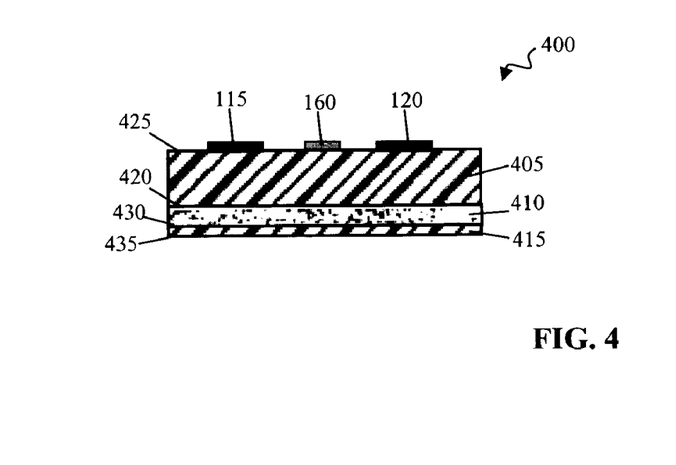
FIGS. 4, 5 are schematic representations of cross-sections of sheet-like materials that can be used to form a base of apparatus for implanting one or more medical devices.

FIG. 4 is a schematic representation of cross-section 4-4 of a sheet-like material 400 that can be used to form base 105 before deployment in implanting medical devices. Material 400 includes a base layer 405, an adhesive layer 410, and a peel-away backing layer 415. Base layer 405 can be a polymeric material that is formed into a sheet having a pair of generally planar outer surfaces 420, 425. Base layer 405 can be flexible in that medical personnel can manually conform material 400 to the contours of a patient's anatomy. For example, base layer 405 can include a polyester, a nylon, a paper, a polypropylene, a polyurethane foam, and/or a stainless steel foil and can have a thickness of, e.g., 0.1 to 3 mm. Visual indicia (such as visual indicia 115, 120) and radiographic indicia (such as radiographic indicia 160) can be affixed to surface 425 of base layer 405.

All or a portion of surface 420 of base layer 405 can be coated with adhesive layer 410. Adhesive layer 410 can include adhesive that adheres both to base layer 405 and to human skin but is removable from human skin when pulled. Adhesive layer 410 can be biocompatible in that contact with human skin does not result in an adverse allergic or other reaction. Adhesive layer 410 can be flexible in that medical personnel can manually conform material 400 to the contours of a patient's anatomy without excessive interference from adhesive layer 410. In some implementations, adhesive layer 410 can be made from medical grade acrylic adhesive.

Peel-away backing layer 415 is a sheet having a pair of generally planar outer surfaces 430, 435. Surface 430 can removably contact adhesive layer 410 so that peel-away backing layer 415 can be peeled away and adhesive layer 410 exposed for deployment on a patient's anatomy. In some implementations, peel-away backing layer 415 can be made from Kraft release liner and can be, e.g., 0.1-2 mm thick.

Figure 5:
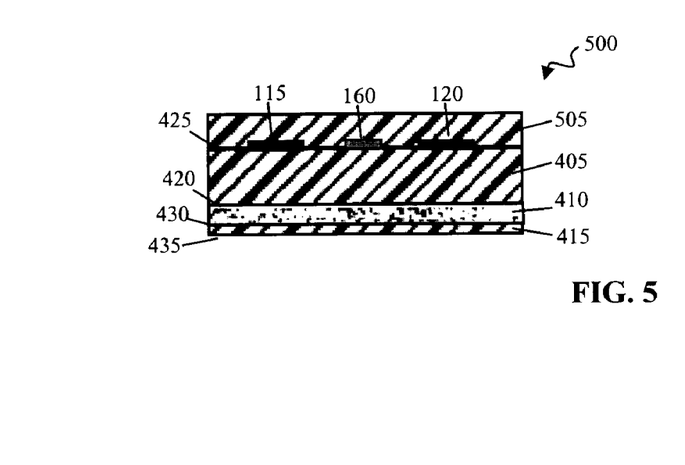

FIG. 5 is a schematic representation of cross-section 5-5 of a sheet-like material 500 that can be used to form base 105 before deployment in implanting medical devices. In addition to base layer 405, adhesive layer 410, and peel-away backing layer 415, material 500 includes a cover layer 505. Cover layer 505 can be a transparent polymeric material that covers surface 425 of base layer 405, along with any visual and radiographic indicia thereon, such as visual indicia 115, 120 and radiographic indicium 160. Cover layer 505 can shield such indicia from damage during the handling of apparatus 100. Cover layer 505 can be flexible in that medical personnel can manually conform material 500 to the contours of a patient's anatomy without excessive interference from cover layer 505. Cover layer 505 can be affixed to surface 425 of base layer 405 using any of a number of different techniques, including, e.g., lamination, roll coating, spray coating, spin coating, dip coating, and the like. In some implementations, cover layer 505 can include a polyester, a nylon, a paper, a polypropylene, a polyurethane foam, and/or a stainless steel foil and can have a thickness of, e.g., 0.1 to 3 mm.

Figure 6:
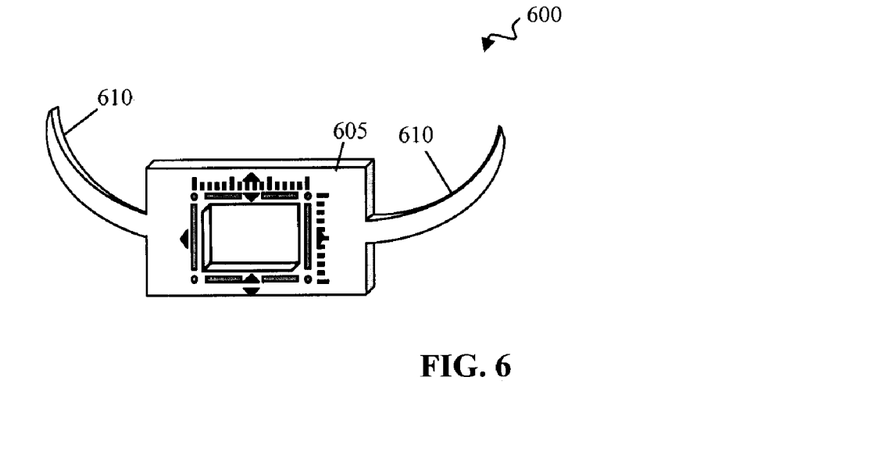

FIG. 6 is a schematic representation of an apparatus 600 for implanting one or more medical devices. Apparatus 600 is a preformed, solid element that retains a shape dimensioned to be aligned with anatomical features of a patient. For example, apparatus 600 can include a base 605 and a pair of preformed alignment arms 610. Base 605 can be a generally flat member that is shaped to mimic the contours of a patient's neck. Base 605 can define a surgical cutout and include visual indicia and radioscopic indicia to guide the implantation of one or more medical devices.

Alignment arms 610 extend outward from base 605 and are shaped to mimic the contours of a patient's anatomy. Alignment arms 610 are shaped so that proper arrangement of arms 610 relative to anatomical features positions apparatus 600, and any indicia thereon, to guide a proper implantation of one or more medical devices. For example, alignment arms 610 can be aligned and dimensioned so that when they are arranged to contact the mastoid processes of a patient, apparatus 600 and indicia thereon can guide medical personnel in the proper implantation of one or more medical devices in the dorsal side of the neck of a patient.

Figure 7:
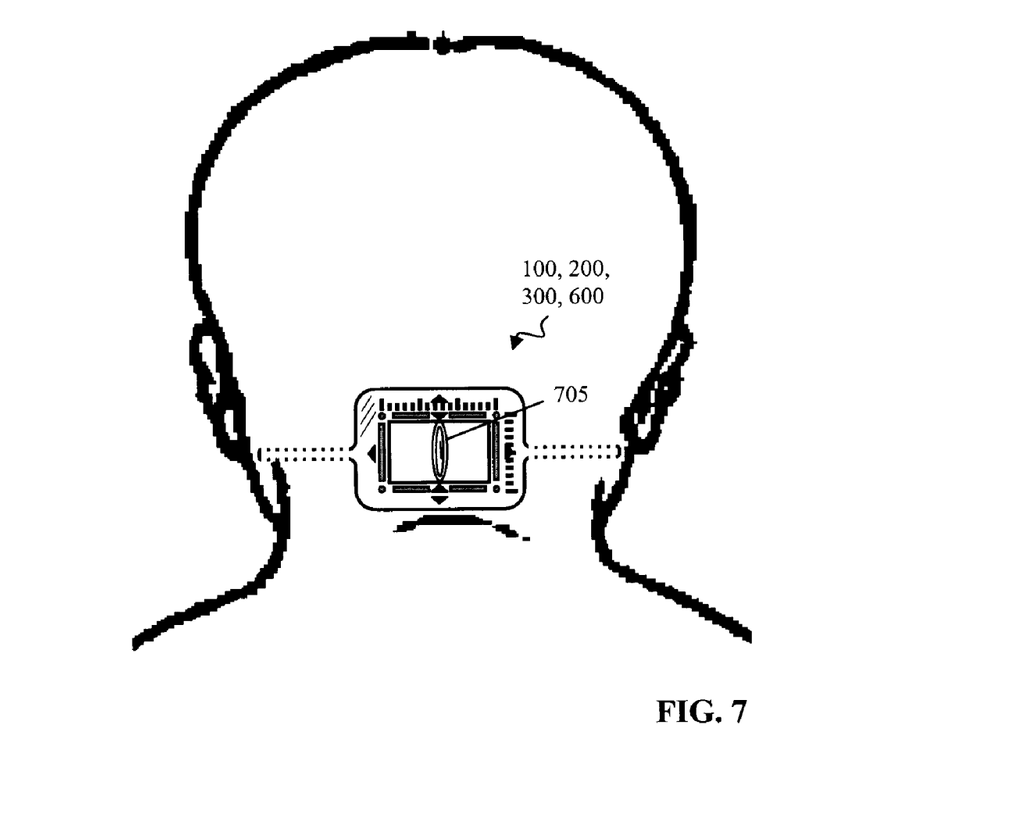
FIGS. 7 and 8 are schematic representations of a deployment of an apparatus for implanting one or more medical devices.
Figure 8:
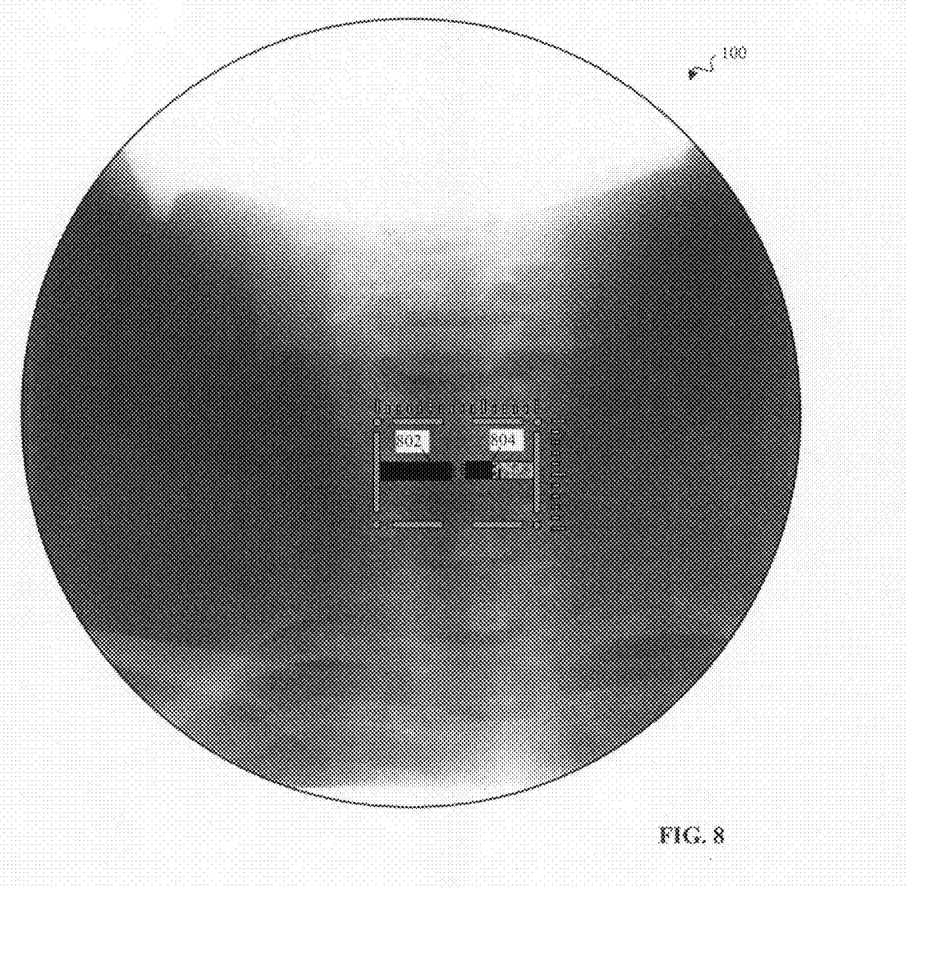

FIGS. 7 and 8 are schematic representations of a deployment of an apparatus, such as apparatus 100, 200, 300, 600, for implanting one or more medical devices. In particular, FIG. 7 illustrates the deployment as is visible to the naked eye, and FIG. 8 illustrates the deployment under radiographic imaging.

In operation, medical personnel can first prepare an apparatus for implanting one or more medical devices as needed. For example, an apparatus for implanting medical devices can be cleaned and sterilized. As another example, a peel-away backing can be removed from such an apparatus so that an adhesive layer can adhere to a patient.

The apparatus for implanting medical devices can be arranged relative to anatomical features of a patient. For example, alignment tabs and/or arms can be aligned with anatomical features such as the mastoid processes to properly position a base, along with any surgical cutouts, visual indicia, and/or radioscopic indicia thereon. As another example, visual indicia and/or radioscopic indicia can be aligned with anatomical features such as the intermastoid line and the midline of a patient to properly position a base, along with any surgical cutouts, visual indicia, and/or radioscopic indicia thereon. After it is arranged properly, the apparatus for implanting medical devices can be adhered to the patient, e.g., by pressing the apparatus against the patient's skin.

Using the guidance provided by properly aligned visual and/or radioscopic indicia, medical personnel can implant one or more medical devices. For example, a proper location for an incision can be identified from visual indicia. As another example, the proper insertion path or depth for a cannula that is used to implant a medical device can be identified from radioscopic indicia. As another example, dissection trajectories can be identified from visual indicia. As yet another example, the proper arrangement of a charging element of an implanted medical device can be confirmed using visual and/or radiographic indicia. A further example is illustrated in FIG. 7, which shows the positioning of an incision 705 relative to surgical cutouts, visual indicia, and radioscopic indicia on a base. A yet further example is illustrated in FIG. 8, which shows the positioning of implanted medical devices 802, 804 relative to radioscopic indicia on the base.

In some implementations, an apparatus for implanting medical devices include visual and radioscopic indicia for positioning of multiple devices relative anatomical targets. For example, an apparatus for implanting medical devices can be placed on a patient. Medical personnel can use a percutaneous stimulating needle to locate a nerve and then reposition the apparatus for implanting medical devices based on the location of the nerve identified using percutaneous stimulation. Even if the percutaneous needle is subsequently removed, the positioning of the apparatus for implanting medical devices can be used to position and/or implant other medical devices. For example, a medical device with stimulating electrodes can be implanted at the site identified using percutaneous stimulation.

In some implementations, medical personnel can use one or more indicia on an apparatus for implanting medical devices as a guide for marking the skin of a patient. For example, the skin of a patient can be marked using visual and/or radioscopic indicia such as ink. Such marks can then be used in implanting a medical device, even after the apparatus for implanting medical devices has been removed from the skin. At times, the apparatus for implanting medical devices can be returned to the skin after an incision is made and/or a device is implanted. Using the visual and/or radioscopic indicia on the apparatus for implanting medical devices, medical personnel can confirm that an incision and/ or implanted device is properly positioned.

After implantation, the one or more implanted medical devices can function unhindered by misplacement or misalignment. For example, microstimulators can stimulate nerve or cells. Microstimulators implanted in the dorsal side of the neck can stimulate nerves for treating migraine headaches. As another example, an implanted medical device that includes a charging element can be charged effectively, e.g., when an electric and/or magnetic field is generated in the vicinity of the implanted medical device using a device positioned outside of the patient's skin.

Figure 9A:
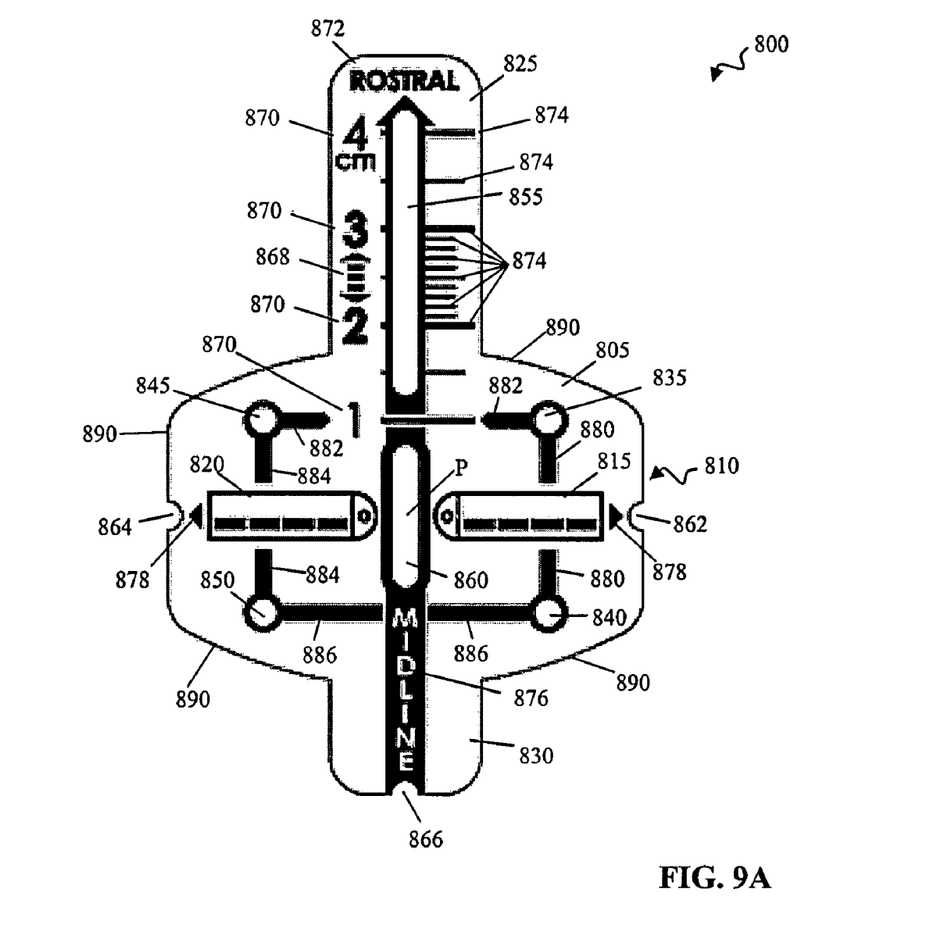
FIG. 9A is a schematic representation of an apparatus for implanting one or more medical devices.

FIG. 9A is a schematic representation of an apparatus 800 for implanting one or more medical devices. Apparatus 800 includes a base 805 that can be positioned to align indicia thereon with anatomical features of a patient and/or a medical device during or after implantation.

Base 805 includes a diagram 810 that includes representations 815, 820 or medical devices. Diagram 810 is visible to the naked eye and can illustrate the proper arrangement of medical devices before, during, or after implantation to medical personnel.

A pair of alignment tabs 825, 830 extend outwardly from base 805. As shown, alignment tab 825 is longer than alignment tab 830 and hence extends further away from base 805. In operation, alignment tabs are to be aligned longitudinally along the midline of a patient and can be positioned relative to the occipital protuberance, as discussed further below.

Base 805 includes a collection of surgical cutouts 835, 840, 845, 850, 855, 860, a collection of perimeter features 862, 864, 866, a collection of visual indicia 868, 70, 872, 874, 876, 878, and a collection of combined visual and radioscopic indicia 880, 882, 884, 886.

Surgical cutouts 835, 840, 845, 850, 855, 860 traverse base 805. Surgical cutouts 835, 840, 845, 850 are generally circular in shape and are dimensioned to pass the tip of a sterile skin marker so that a collection of generally circular marks can be made on the skin of a patient when base 805 is properly positioned. Surgical cutouts 855, 860 are generally elongate in shape and are also dimensioned to pass the tip of a sterile skin marker so that a pair of generally elongate marks can be made on the skin of a patient when base 805 is properly positioned.

Perimeter features 862, 864, 866 are inwardly sloping depressions along a perimeter 890 of base 805. Perimeter features 862, 864, 866 are dimensioned to receive the tip of a sterile skin marker so that a collection of generally marks can be made on the skin of a patient when base 805 is properly positioned, as discussed further below.

Visual indicia 868, 870, 872, 874, 876, 878 are markings on base 105 that are visible to the naked eye. Visual indicia 868, 870, 872, 874, 876, 878 play various roles in the implantation of medical devices. For example, visual indicia 868 generally resembles a two-headed arrow and indicates a range that can be aligned with the occipital protuberance of a patient when base 805 is properly positioned with respect thereto. Visual indicia 870 is a collection of one or more numeric indicia that indicate a number of units distance from a center point P which is in the middle of cutout 860. Visual indicia 872 is a collection of one or more alphanumeric indicia (i.e., the word "ROSTRAL") that guides medical personnel in the proper alignment of base 805 relative to anatomical features of a patient. In particular, visual indicia 870 indicates that alignment tab 825 is to be positioned rostrally to the occipital protuberance of a patient when base 805 is properly positioned with respect thereto.

Visual indicia 874 is a collection of fine and coarse ruler marks that demarcate distance units from center point P. Visual indicia 876 is a collection of one or more alphanumeric indicia (i.e., the word "MIDLINE") that guides medical personnel in the proper alignment of base 805 relative to anatomical features of a patient. In particular, visual indicia 876 indicates a line that is to be positioned along the midline of a patient when base 805 is properly positioned with respect thereto. Visual indicia 878 is a pair of generally triangular features that indicate the intermastoid line on the dorsal side of the neck of a patient when base 805 is properly positioned with respect thereto.

Combined visual and radioscopic indicia 880, 882, 884, 886 are visible both to the naked eye and under radioscopic imaging to guide medical personnel in the proper implantation of one or more medical devices. Indicia 880, 882, 884, 886 form a generally rectangular frame around point P.

Figure 9B:
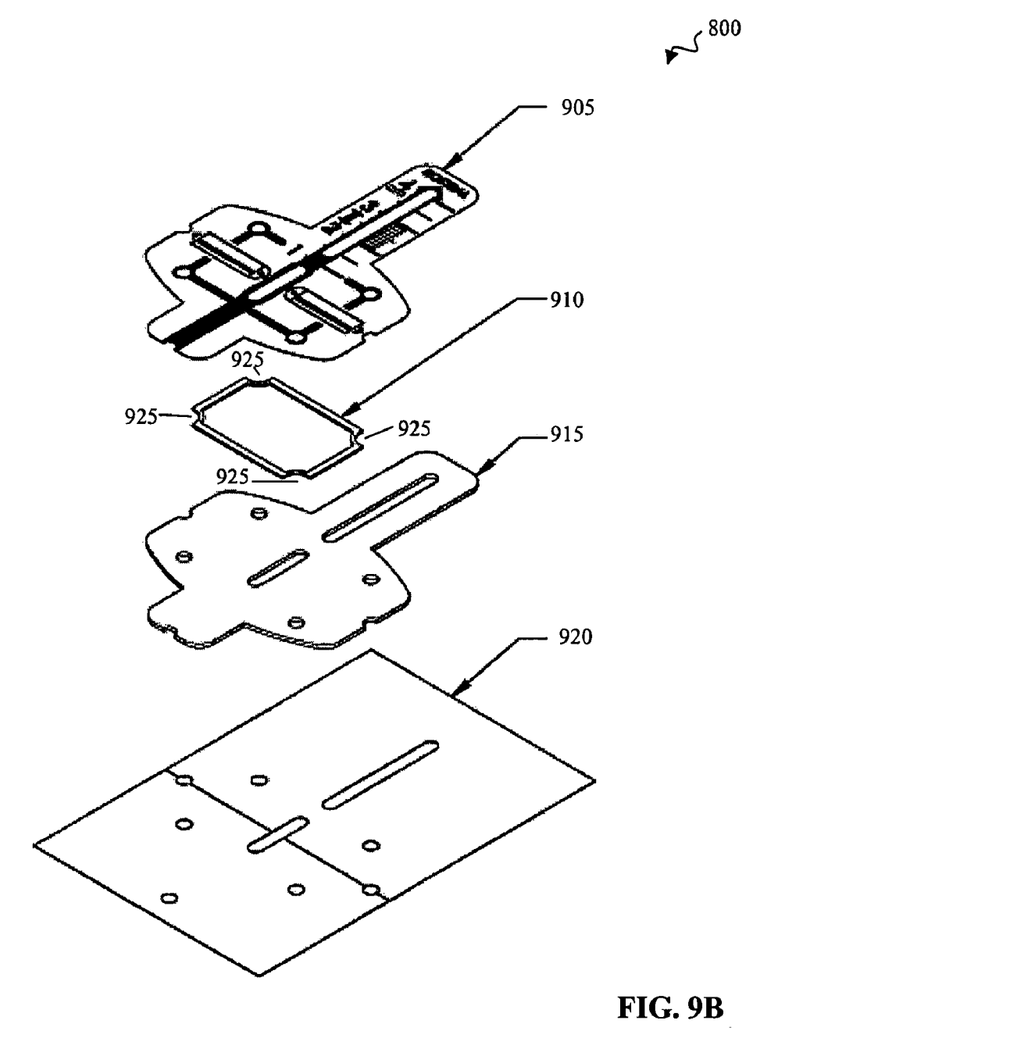
FIG. 9B is a schematic representation of various layers that can be assembled to form the apparatus of FIG. 9A.

FIG. 9B is a schematic representation of various layers 905, 910, 915, 920 that can be assembled to form apparatus 800 (FIG. 9A). Top layer 905 is a polymeric film that has been marked with a laser to form diagram 810, visual indicia 868, 870, 872, 874, 876, 878, and visually-apparent aspects of combined visual and radioscopic indicia 880, 882, 884, 886

(FIG. 8). In some implementations, the polymeric film of top layer 905 is a 2 mil thick white polyester layer. Top layer 905 can be coated with an adhesive, such as P-34 adhesive, on its underside.

Insert layer 910 is a generally rectangular metallic frame insert that includes rounded edges 925. Rounded edges 925 are dimensioned and positioned to allow surgical cutouts 835, 840, 845, 850 to pass the tip of a sterile skin marker when layers 905, 910, 915, 920 have been assembled to form apparatus 800 (FIG. 8). In some implementations, insert layer 910 can be formed from a lead foil or a low density polyethylene composite such as RTP 799 AX 113633AZ (RTP Company, Winona, Minn.).

Substrate layer 915 is a foam polymeric sheet substrate. In some implementations, substrate layer 915 can be formed of a 1/32 inch thick polyethylene layer, such as Voltek cross-linked polyethylene #60E-white (Voltek division of Sekesui America Corporation, MA). In some implementations, substrate layer 915 can be coated with a medical grade acrylic adhesive on its underside, such as Solutia #RA788 (Solutia, St. Louis, Mo.).

Liner layer 920 is a generally rectangular backing layer that can be peeled away from an adhesive on the underside of substrate layer 915. In some implementations, liner layer can be formed from a split release liner such as HDPE and bleach Kraft paper.

Figure 10:
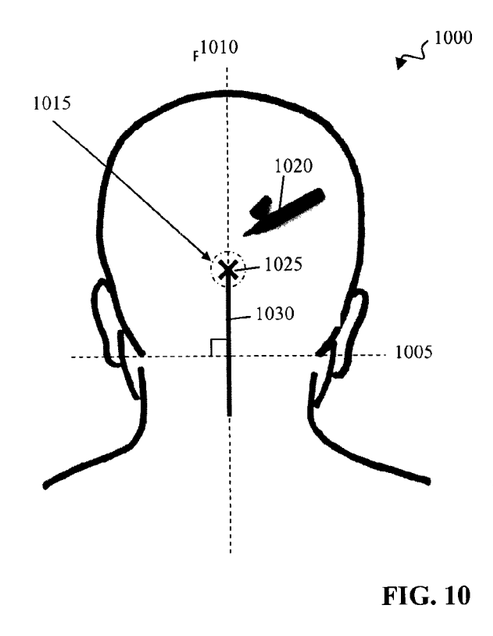
FIGS. 10-15 are schematic representations of a deployment of an apparatus for implanting one or more medical devices.

FIGS. 10-15 are schematic representations of a deployment of an apparatus, such as apparatus 800, for implanting one or more medical devices. In particular, FIG. 10 illustrates the dorsal side 1000 of a patient. The patient's intermastoid line 1005, midline 1010, and occipital protuberance 1015 are all found on dorsal side 1000.

As shown in FIG. 10, using a sterile skin marker 1020, a surgeon or other medical personnel can mark the apex of occipital protuberance 1015 with an "X" mark 1025. Based on the location of occipital protuberance 1015, the surgeon can draw a line 1030 caudally along the midline 1010. Line 1030 can be, e.g., between 7 and 10 cm long.

Figure 11:
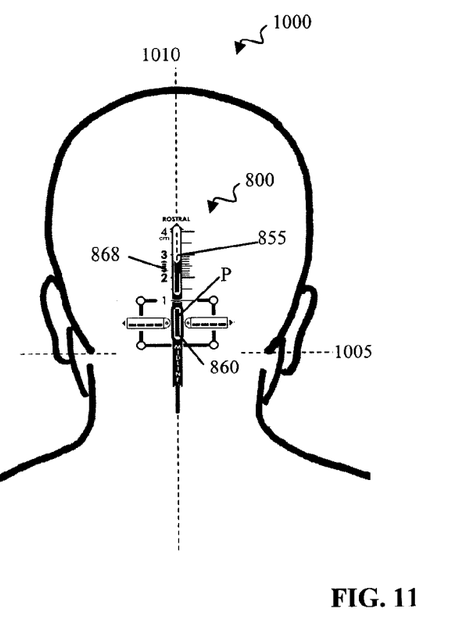

As shown in FIG. 11, after any liner has been removed from apparatus 800, the surgeon can align surgical cutouts 855, 860 of apparatus 800 with line 1030 along the patient's midline. Moreover, visual indicia 868 can be aligned with "X" mark 1025. While maintaining this alignment, apparatus 800 can be pressed against the skin of the patient to position center point P in cutout 860 approximately 2-3 cm caudal to the occipital protuberance.

Figure 12:
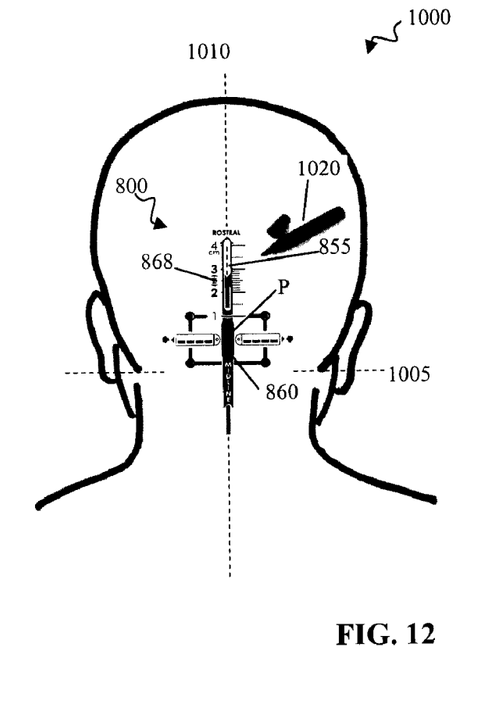
Figure 13:
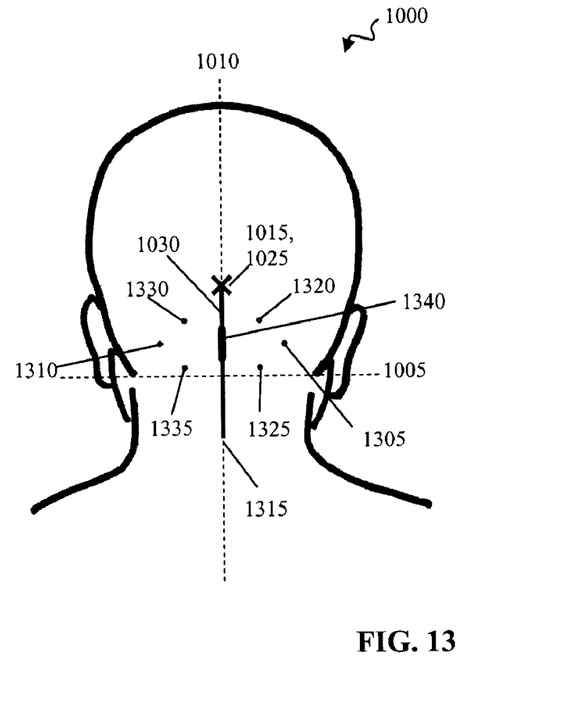

As shown in FIG. 12, under the guidance of apparatus 800, a surgeon can add additional marks to the skin of the patient using sterile skin marker 1020. In particular, as shown in FIG. 13, a surgeon can make a collection of marks 1305, 1310, 1315 based on the positions of perimeter features 862, 864, 866, respectively, and a collection of marks 1320, 1325, 1330, 1335 based on the positions of surgical cutouts 835, 840, 845, 850, respectively. The surgeon can also embolden line 1030 using a mark 1340 using cutout 860. In some implementations, apparatus 800 can be removed after marks 1305, 1310, 1315, 1320, 1325, 1330, 1335, 1340 have been made.

Figure 14:
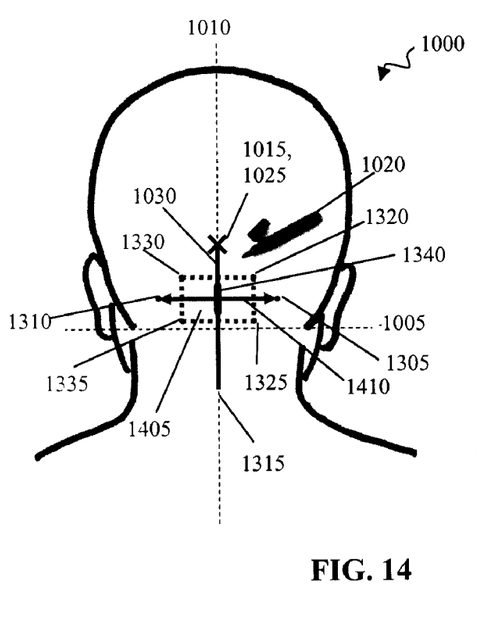

As shown in FIG. 14, using sterile skin marker 1020, the surgeon can connect marks 1320, 1325, 1330, 1335 to form a charging window 1405 that demarcates a charging window. Charging window 1405 is the boundary within which acceptable charging of an implantable medical device can occur. Further, the surgeon can draw a transverse line 1410 between marks 1305, 1310 to further assist the surgeon in the implantation of a medical device.

Figure 15:
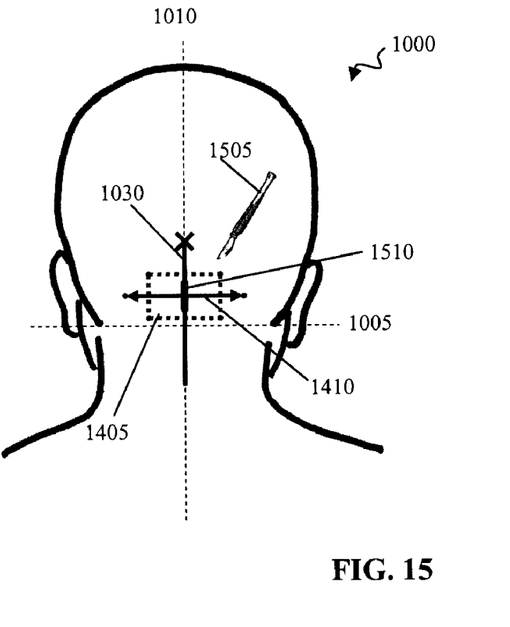

As shown in FIG. 15, using a scalpel 1505, the surgeon can create an incision 1510 along midline 1010 at the former position of mark 1340 within charging window 1405. In some implementations, incision 1510 is about 1.5 cm long and can be used to implant one or more medical devices. In some implementations, after implantations, apparatus 800 can be repositioned using one or more marks on the dorsal side of the patient to verify that any implanted device is positioned and aligned properly. The verification can be performed, e.g., via palpation and/or radiographic imaging.

A number of implementations have been described. Nevertheless, it will be understood that various modifications may be made. For example, an apparatus for implanting one or more medical devices need not include a surgical cutout at all. Rather, features on a perimeter of an apparatus for implanting medical devices can identify an anatomical location that is relevant to an implantation. As another example, a surgical membrane such as TAGADERM or IOBAN (3M, St. Paul, Minn.) can identify an anatomical location that is relevant to an implantation. A surgical knife or other tool can be used to pierce such a surgical membrane after arrangement of the apparatus.

As another example, an apparatus for implanting one or more medical devices need not be adhered to a patient during implantation. For example, an apparatus for implanting one or more medical devices can be strapped, tied, sutured to, or pressed against a patient during implantation. As another example, an apparatus for implanting one or more medical devices can be made from paper, metal, or other materials.

As yet another example, alignment tabs and arms can extend in directions other than those illustrated. For example, an alignment tab or arm can extend into a surgical cutout. As another example, an alignment tab or arm can extend to another anatomical feature, such as the occipital protuberance.

As yet another example, an apparatus for implanting one or more medical devices can be used to mark a patient. The marks can guide the implantation of one or more medical devices. For example, an apparatus can include transferable elements that can be transferred from the apparatus to the skin of a patient to mark the patient after arrangement of the apparatus. The transferred elements can thus create visual and/or radiographic indicia on the patient. As another example, an apparatus can include holes or other guide elements that can guide the drawing of marks on the skin of a patient. The drawn marks can thus create visual and/or radiographic indicia on the patient.

As yet another example, a wide variety of numeric and alphanumeric indicia can be used on an apparatus for implanting one or more medical devices. Examples of such indicia include "charging window," "intermastoid line," "incision," "align occipital protuberance here," and the like.

Accordingly, other implementations are within the scope of the claims.

What is claimed is:

1. An apparatus for implanting a medical device, comprising:
   a flexible base member that can be flexed manually to conform to a contour of an anatomy, the base member including a surgical cutout and at least one cutout alignment radioscopic indicium configured and arranged to assist a practitioner in aligning the cutout of the base member with a desired implantation site, wherein the at least one radioscopic indicium has a characteristic such that, under radioscopic imaging, passage of a skin-penetrating electromagnetic radiation is hindered to an extent that is distinguishable from a hindrance of the electromagnetic radiation by another portion of the base member, wherein the base member further comprises an illustration of the medical device, spaced apart from the at least one cutout alignment radioscopic indicium, with markings indicating proper alignment of the medical device when implanted according to the illustration.

2. The apparatus of claim 1, wherein the base further comprises at least one set of ruler marks configured and arranged for assisting in placement of the medical device for implantation.

3. The apparatus of claim 1, wherein the medical device includes a charging element for accumulating potential energy at the medical device and the illustration of the medical device on the base member comprises a marking selected to correspond to a feature of the charging element that indicates proper alignment of the charging element of the medical device when implanted according to the illustration.

4. The apparatus of claim 1, wherein the base member comprises a sheet-like polymeric material.

5. The apparatus of claim 1, further comprising an adhesive to removably adhere the base member to the contour of the anatomy.

6. The apparatus of claim 1, wherein the at least one radioscopic indicium comprises at least one visual indicia configured and arranged to align with an anatomical feature when the surgical cutout is positioned relative to an anatomical location that is relevant to an implantation.

7. The apparatus of claim 1, wherein the at least one radioscopic indicium comprises at least one indicium that demarcates a boundary of the surgical cutout on the base member.

8. The apparatus of claim 1, further comprising an alignment tab that extends outward from the base member and that is dimensioned so that when the alignment tab is properly arranged relative to an anatomical feature of a patient, the base can guide the implantation of the medical device.

9. The apparatus of claim 1, wherein the radioscopic indicium comprises a plurality of dots demarcating corners of the surgical cutout.

10. The apparatus of claim 1, wherein the at least one radioscopic indicium comprises at least one visual, alphanumeric indicia configured and arranged to guide proper alignment of the base member relative to an anatomical feature.

11. The system apparatus of claim 10, wherein the at least one visual, alphanumeric indicia comprises a word indicating a line that is to be positioned along a midline of a patient.

12. A method comprising:
arranging the apparatus of claim 1; and
implanting, under guidance of the apparatus, the medical device, wherein the medical device includes a charging element for accumulating potential energy at the medical device and the guidance of the apparatus arranges the charging element for the effective accumulation of the potential energy.

13. The method of claim 12, further comprising manually flexing the apparatus to conform to a contour of an anatomy.

14. The method of claim 12, wherein implanting the medical device under the guidance of the apparatus comprises radioscopically imaging the medical device and the radioscopic indicium of the apparatus.

15. The method of claim 14, wherein radioscopically imaging the medical device comprises confirming that the charging element is arranged properly.

16. The method of claim 12, wherein arranging the apparatus comprises aligning the radioscopic indicium with the anatomical feature.

17. The method of claim 12, wherein arranging the apparatus comprises aligning a mechanical element with the anatomical feature.

18. The method of claim 17, wherein aligning the mechanical element comprises contacting an outwardly-extending arm to the anatomical feature.

19. The method of claim 12, wherein arranging the apparatus comprises aligning, with the anatomical feature, a preformed, solid element that retains a shape.

20. A system comprising;
an implantable medical device; and
the apparatus of claim 1, wherein the illustration is of the medical device with markings indicating proper alignment of the medical device when implanted according to the illustration.

21. The system of claim 20, wherein the medical device includes a charging element.

* * * * *